US009173671B2

(12) United States Patent
Smith et al.

(10) Patent No.: US 9,173,671 B2
(45) Date of Patent: Nov. 3, 2015

(54) TISSUE RESECTION DEVICE AND RELATED METHODS OF USE

(71) Applicants: Paul Smith, Smithfield, RI (US); Samuel Raybin, Marlborough, MA (US); Naroun Suon, Lawrence, MA (US); Gary Kappel, Acton, MA (US)

(72) Inventors: Paul Smith, Smithfield, RI (US); Samuel Raybin, Marlborough, MA (US); Naroun Suon, Lawrence, MA (US); Gary Kappel, Acton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 316 days.

(21) Appl. No.: 13/728,078

(22) Filed: Dec. 27, 2012

(65) Prior Publication Data
US 2014/0012255 A1    Jan. 9, 2014

Related U.S. Application Data

(60) Provisional application No. 61/581,735, filed on Dec. 30, 2011.

(51) Int. Cl.
| | | |
|---|---|---|
| *A61B 17/32* | (2006.01) | |
| *A61B 17/3205* | (2006.01) | |
| *A61B 17/00* | (2006.01) | |
| *A61B 18/00* | (2006.01) | |
| *A61B 17/30* | (2006.01) | |
| *A61B 18/14* | (2006.01) | |

(52) U.S. Cl.
CPC ......... *A61B 17/320016* (2013.01); *A61B 17/32* (2013.01); *A61B 17/32056* (2013.01); *A61B 18/00* (2013.01); *A61B 18/1492* (2013.01); *A61B 2017/003* (2013.01); *A61B 2017/00269* (2013.01); *A61B 2017/306* (2013.01); *A61B 2018/141* (2013.01)

(58) Field of Classification Search
CPC ............... A61B 2017/00269; A61B 17/32056; A61B 17/320016; A61B 17/32
USPC .............................................. 606/42, 45, 170
See application file for complete search history.

(56) References Cited

U.S. PATENT DOCUMENTS

| | | | | |
|---|---|---|---|---|
| 6,352,503 | B1 * | 3/2002 | Matsui et al. | 600/104 |
| 6,942,650 | B1 * | 9/2005 | Schultz et al. | 604/315 |
| 7,789,881 | B2 * | 9/2010 | Weitzner | 606/47 |
| 2005/0119524 | A1 * | 6/2005 | Sekine et al. | 600/114 |
| 2005/0261674 | A1 | 11/2005 | Nobis et al. | |
| 2006/0064113 | A1 | 3/2006 | Nakao | |
| 2007/0260112 | A1 * | 11/2007 | Rahmani | 600/104 |
| 2010/0256523 | A1 * | 10/2010 | Uznanski et al. | 600/565 |

OTHER PUBLICATIONS

International Search Report for related International Application No. PCT/US2012/071764, mailed May 13, 2013, (4 pages).

\* cited by examiner

*Primary Examiner* — Catherine Voorhees
(74) *Attorney, Agent, or Firm* — Bookoff McAndrews, PLLC (57) ABSTRACT

A device configured to facilitate resection of tissue. The device may include a proximal end configured to be secured to a distal portion of an introduction sheath and a distal end defining an opening that may communicate with a channel extending between the proximal and distal ends. The opening may be defined by at least one straight edge.

20 Claims, 8 Drawing Sheets

FIG. 8D

TISSUE RESECTION DEVICE AND RELATED METHODS OF USE

CROSS-REFERENCE TO RELATION APPLICATION

This application claims the benefit of priority from U.S. Provisional Application No. 61/581,735, filed Dec. 30, 2011, which is herein incorporated in its entirety.

FIELD OF THE INVENTION

This disclosure relates generally to systems and methods for resecting tissue. More particularly, embodiments of the present disclosure relate to systems for minimally invasive endoscopic mucosal resection.

BACKGROUND OF THE INVENTION

Organ walls are composed of several layers: the mucosa (the inner surface layer), the submucosa, the muscularis (muscle layer), and the serosa (connective tissue layer). In cases of gastrointestinal, colonic, and esophageal cancer, for example, small polyps or cancerous masses may form along the mucosa and often extend into the lumens of the organs. Conventionally, that condition has been treated by cutting out or otherwise removing a portion of the affected organ wall. This procedure, however, often may cause extensive discomfort to patients and may pose health risks. Recently, physicians have adopted a minimally invasive technique known as endoscopic mucosal resection (EMR), which removes the cancerous or abnormal tissue while keeping the walls of the organ intact. EMR may also assist in removing any undesired tissue, even if such tissue is not abnormal or diseased.

EMR is generally performed with an endoscope, which, in some embodiments, may be a long, narrow elongated member having channels equipped with an illumination source, an imaging device, and/or other instruments. In some instances of EMR treatment, the endoscope may be passed down the throat, guided through the rectum, or passed through other natural body openings to reach the tissue targeted for resection. The distal end of the endoscope may further include a cutting guide (e.g., a cap) and a cutting device (e.g., a wire loop) introduced through an endoscopic channel towards the guide. Once there, suction may be applied through the elongate member, which draws the targeted tissue towards and into the cutting guide. Alternatively, the targeted tissue may be drawn into the cap by any suitable means. When the tissue is sufficiently drawn into the cap, the cutting device may close around the tissue, thereby resecting it from the organ wall. Subsequently, excised tissue may be extracted for examination, biopsy, or disposal.

In addition, conventional EMR caps may be circular, oblique, elliptical, or any combination thereof. These EMR caps may consequently have resection openings of similar geometries. During procedures where a large area of tissue is to be removed, separate circular cuts are generally utilized to remove the target tissue. However, due to the risk of perforating the underlying muscularis layer, caution is exercised and overlapping cuts are avoided. By avoiding overlapping circular cuts, areas between the adjacent circular cuts are often not removed. These areas of potentially undesired tissue may be left behind by the conventional circular EMR caps, may require additional procedures or contribute to the development of metastatic cancer, if the tissue left behind is diseased.

Therefore, there exists a need for an improved endoscopic mucosal resection tool that effectively resects targeted tissue without damaging the surrounding tissue or muscle layers of the organ; and that allows for more complete, efficient removal of larger areas of tissue.

SUMMARY OF THE INVENTION

Embodiments of the present disclosure provide a device for resecting an undesired mass from a patient's body using a minimally invasive surgical system.

One embodiment of the present disclosure is directed to a resection device configured to facilitate resection of tissue. The resection device may include a proximal end extending from a distal portion of a flexible member and a distal end including an opening that communicates with one or more channels extending between the proximal and distal ends. The opening may include at least one straight edge.

In various embodiments, the resection device may include one or more of the following additional features: the resection device may be a cap; the opening may be disposed in a plane that is angled relative to a longitudinal axis of the resection device; the distal end of the resection device may be configured to move relative to the proximal end of the resection device; a cutting device configured to cut tissue disposed adjacent the resection device; the cap assembly may include a flexible portion disposed between the proximal and distal ends; the cutting device may include a wire spanning a width of the opening; the wire may be configured to conduct energy to the tissue; the proximal end may define a cavity for receiving an end of the flexible member; and the at least one straight edge includes a plurality of straight edges.

Another embodiment of the present disclosure is directed to a device for resecting tissue from a body. The device may include an elongate member having a proximal end, a distal end, and a lumen extending therebetween. The distal end of the elongate member may include an opening adapted to be placed proximate the tissue. The opening may include at least one straight edge, and the opening may be disposed in a plane that is angled relative to a longitudinal axis of the cap assembly.

In various embodiments, the device may include one or more of the following additional features: the distal end of the elongate member may include a cap that defines the opening with at least one straight edge, wherein the cap includes a cavity in communication with the opening; the opening may be one of rectangular, square, or rhombic in shape; the opening may be side facing and distal facing; a cutting device may be configured to cut tissue along at least one straight line of dissection; the cutting device may include a wire spanning the opening; the cap may include a flexible member configured to allow a distal portion of the cap to move relative to a proximal end of the cap; and the distal end of the elongate member may be configured to pivot relative to a remainder of the elongate member.

In another embodiment, the present disclosure is directed to a method for resecting tissue from a body. The method may include inserting a device into a body cavity. The device may include an elongate member having a proximal end, a distal end, and a lumen extending therebetween. Further, the distal end may include a distal end opening, wherein the distal end opening includes at least one straight edge, and wherein the distal end opening may be angled relative to a longitudinal axis of the elongate member, and at least one channel extending between the proximal and distal ends. Further, a cutting device configured to cut tissue, the cutting device being adapted for placement adjacent the distalmost edge of the opening in the distal end. The method may also include pulling the tissue into the channel of the cap, and resecting the tissue with the cutting device.

In one embodiment, the step of resecting the tissue may include moving the cutting device relative to the opening. In addition, the pulling step may include introducing suction force.

Additional objects and advantages of the present disclosure will be set forth in part in the description which follows, and in part will be obvious from the description, or may be learned by practice of the embodiments disclosed herein. The objects and advantages of this disclosure will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary embodiments of the present disclosure and together with the description, serve to explain the principles of the disclosure.

DESCRIPTION OF THE EMBODIMENTS

Reference will now be made in detail to embodiments of the present disclosure, an example of which is illustrated in the accompanying drawings. Wherever possible, the same reference numbers will be used throughout the drawings to refer to the same or like parts. The term "distal" refers to the end farthest away from a medical professional when introducing a device in a patient. By contrast, "proximal" refers to the end closest to the medical professional when placing a device in the patient.

Overview

Embodiments of the present disclosure relate to devices and methods for resecting and extracting cancerous, foreign, or otherwise undesirable or unwanted tissue from a patient's body. For example, the device may remove cancerous polyps or lesions from the mucosal walls of the colon, esophagus, stomach, or duodenum. A physician may also desire to resect tissue in order to conduct a biopsy or other examination. It should be understood that the resection device may perform the functions of both resecting and retrieving, but for convenience, the term "resection device" will be used throughout this application. In addition, "banding" as used in this disclosure, refers to a medical procedure that uses elastic bands to constrict blood supply to lesions, polyps, organs or other tissues, so that the ligated tissue eventually dies and sloughs away from the supporting tissue. "Banding" may also refer to the capture and elevation of tissue for subsequent resection and/or snaring.

For conducting such procedures, embodiments of the resection device described in the present disclosure include a cutting guide, such as, e.g., an EMR cap assembly configured to be coupled to a distal portion of any suitable elongated member or other introduction sheath, such as an endoscope, for ensnaring or banding, cauterizing/severing, and/or extracting tissue, such as a polyp. In general, the cutting guide provides a cavity for capturing the undesired tissue. The EMR cap assembly may include a proximal end, a distal end, and at least one channel defined therein. The distal end may include an opening in communication with the channel. In accordance with embodiments of the present disclosure, the distal end opening may include at least one straight edge defining the opening periphery. In an embodiment, the distal end of the cap assembly may be tapered relative to the proximal end of the cap assembly to form an angled distal opening. The distal opening may provide a greater resection area than a cross-sectional area of the elongated member or introduction sheath.

For resection purposes, the cap may be positioned within a patient's body at a location proximate undesired tissue, such as, e.g., cancerous, suspect tissue, or otherwise unwanted tissue. The tissue may be drawn through the distal opening into the cap using, for example, suction. Subsequently, a cutting device, including, for example, a snare or wire loop, which may or may not include cauterizing capabilities, may resect the tissue just beyond the distal end of the cap or be pulled across the base of the cap to separate the drawn-up tissue from the remainder of the patient.

The cutting guide of the present disclosure resects tissue with a straight side, thereby allowing for subsequent cuts to be tessellated next to one another. That is, subsequent adjacent tissue removal may be accomplished by placing a straight side of the cutting guide proximate to a straight side of a resected section. Adjacent tissue sections may be continually removed in this manner without leaving undesired tissue behind. Providing resected sections with at least one straight side minimizes the need to overlap sections to achieve complete removal of undesired tissue.

Exemplary Embodiments

Figure 1:
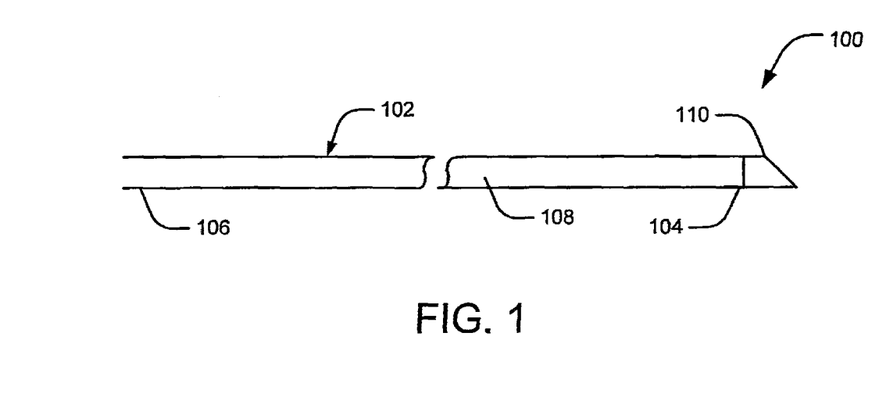
FIG. 1 is an exemplary resection device according to an embodiment of the present disclosure.

FIG. 1 is a view of an embodiment of a resection device 100 for resecting polyps, lesions, or otherwise unwanted tissue from the walls of an organ. The resection device 100 includes an elongate member 102 having a proximal end 106, distal end 104, and a lumen 108 extending between the proximal and distal ends 106, 104. Proximal end 106 may be coupled to a handle (not shown), while distal end 104 may include an opening in communication with lumen 108. In addition, distal end 104 may be configured to be coupled to a suitable cutting guide, such as, e.g., cap 110.

Elongate member 102 may be an endoscope or any other suitable introduction device or sheath adapted to be advanced into a body lumen. For example, elongate member 102 may include a guide tube, endoscope, guide sheath, flexible member, and/or a catheter. In the illustrated embodiment, elongate member 102 may include one or more channels (not shown), through which, the operator may introduce one or more medical devices to extend out of the distal end of elongate member 102. For example, during a resection, the operator may introduce a suction device into one channel and a cutting device, such as, for example, a snare loop into another channel. Additionally, from time to time during the procedure, the operator may insert a light source, a camera, an injector, or a morcellator within the one or more channels. Elongate member 102 may be any known endoscopic device used for colonoscopy, resectoscopy, cholangioscopy, or mucosal resection, and thus, this device will not be discussed in greater detail.

Cap 110 may be a relatively short, generally hollow member adapted to provide tissue resection. Cap 110 may be configured to fit over the elongated member's distal end 104. Alternatively, cap 110 may be configured to fit into and extend from a lumen of elongated member 102. A portion of cap 110 may have substantially circular cross-sections or cross-sections similar to those of body cavities. Moreover, the size of the cap 110 may vary based on the size of the body lumens in which it operates. For example, if resection device 100 is to be inserted through the urethra of a patient, the diameter of the cap 110 may be very small. Conversely, if the device 100 is inserted through the rectum, the diameter of the cap may be relatively larger. Further, portions of cap 110 may have a generally uniform cross-sectional dimension. Alternatively, the cross-sectional dimensions may vary along its length. For example, the diameter of cap 110 may taper at its distal end to allow convenient insertion into the body. In addition, cap 110 may be transparent or translucent, allowing an operator to view any tissue disposed within cap 110.

In addition, outer surface of the cap 110 may include markings. For example, radiopaque or sonoreflective markings (not shown) may be added to an exterior surface of the cap 110. These markings facilitate detection of a position and/or orientation of the cap 110 within the patient's body, and a surgeon, with the aid of suitable imaging equipment, may track the path followed by the resection device 100 and avoid potential damage to sensitive tissues. Moreover, to inhibit bacterial growth in the body cavity or in the mucosal wall, cap 110 may be coated with an antibacterial coating. The coating may contain an inorganic antibiotic agent, disposed in a polymeric matrix, which adheres the antibiotic agent to the cap's surface. Other suitable coatings may also be applied to one or more surfaces of cap 110. For example, an outer surface of cap 110 may be coated with a lubricious coating. In addition, one or more portions of cap 110 may include suitable atraumatic geometric features, which may facilitate insertion and advancement of resection device 100 with a patient's body.

Any suitable material may be used to fabricate cap 110. For instance, rigid or semi-rigid materials such as metals (including shape-memory materials such as Nitinol), super elastic materials, polymers, resins, or plastics may be used. Cap 110 may also be optically clear, allowing physician to visualize tissue disposed within the hood. Further, a biocompatible material that does not irritate the body lumens may be applied as a coating over the outer surface of cap 110.

Conventionally, the distal end opening of cap 110 is generally circular. For resection purposes, the circular distal end opening is placed adjacent to target tissue 202 (FIG. 2), such as a lesion. Subsequently, at least a portion of tissue 202 may be drawn into the cap 110 using, for example, suction or any other suitable acquisition means, including, but not limited to, needle, forceps, graspers, and/or hooks. With tissue 202 drawn into cap 110, the operator may extend (or retract) a cutting device such as a blade, scissor, snare, cautery, or laser device, and sever a section 206 of the tissue 202. Since the distal end opening of cap 110 is usually circular, the severed section 206 if tissue is consequently circular in nature.

Figure 2:
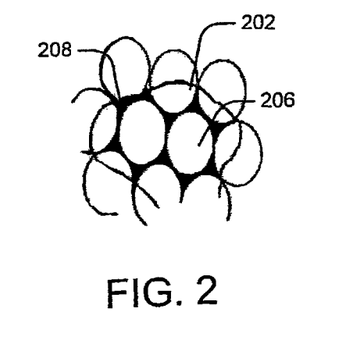
FIG. 2 is a perspective view of a tissue showing conventional circular cuts generally made by conventional circular EMR caps.

Conventionally, for larger lesions, e.g., it may be necessary to remove several circular sections 206 of tissue 202 in order to remove the entire lesion, as shown in FIG. 2. In avoiding overlapping circular cuts, the circular geometry of the cap 110 may not precisely remove tissue sections directly adjacent to one another, and certain "islands" of tissue, depicted by shaded portion 208, between adjacent circularly resected tissues, may be left behind. These areas of undesired tissue left behind by the conventional circular EMR caps may be potentially harmful.

Embodiments of the present disclosure employ a cutting guide, such as, e.g. a novel endoscopic cap assembly, having an altered geometry, designed to remove a lesion completely without residual islands. To this end, the present disclosure employs a cap having a distal end opening with at least one edge of the opening having a straight portion.

Figure 3:
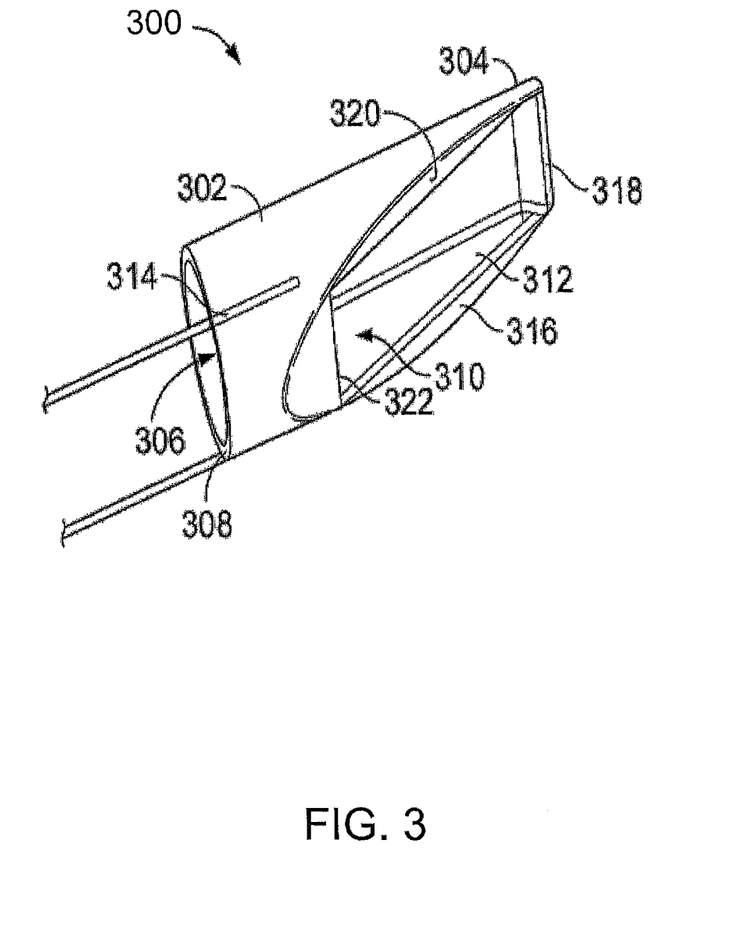
FIG. 3 is a perspective distal end view of a resection device according to an embodiment of the present disclosure.

FIG. 3 illustrates an embodiment of a novel cutting guide in detail. As shown, the cutting guide, which includes an exemplary EMR cap 300, may be a generally hollow member having a proximal end 302, a distal end 304, and a lumen 306 extending between the proximal and distal ends 302, 304. In addition, the proximal end 302 of cap may define a proximal end opening 308 that may be configured to fit over the distal end of an elongated introduction member, such as an endoscope. The distal end 304 of cap 300 may further include a distal end opening 312, which in conjunction with lumen 306 may define a cavity 310.

In one embodiment, distal end 304 may includes a distal end opening 312 having a rectangular cross-section. The distal opening has four straight sides or edges 316, 318, 320 and 322. Where required by given applications, the cross-sectional shape of the distal end opening 312 may be square, rhombic, hexagonal, triangular, semi-circular, quarter circle, or any desired shape having at least edge with a straight portion. In addition, the cross-sectional dimension of the cap may vary along the length of the cap 110. For example, the distal end 304 may be tapered relative to proximal end 302.

In addition, the distal end 304 may be cut on a slant or an angle, other than perpendicular, to the longitudinal axis of cap 300 to provide an elongated distal end opening 312. Because a lesion may be present in a location out of the direct path of an endoscope advancing through the body, the slanted distal end provides for greater surface area contact between the cap's distal end opening 312 and the targeted tissue. It should be understood that the slant angle may vary based on the intended use and application. For example, a narrower body organ, such as the esophagus, calls for a distal opening slanted at a greater angle than for wider body organs, such as the stomach.

Cap 300 may be coupled to distal end 104 of elongate member 102 by suitable coupling mechanism including screw threads, locking projections, interference fit, magnetic connection, for example. In such an embodiment, a proximal portion of cap 300 may include a soft collar made of, e.g., silicone, for coupling with distal end 104 of elongate member 102. Cap 300 may be also be introduced through a working channel of the elongate member 102 and the depth of the cap 300 extending out from the distal end of the elongate member 102 may be adjustable. In such embodiments, an airtight seal may be maintained between cap 300 and elongate member 102. Alternatively, cap 300 may be made integral with the distal end of elongate member 102.

In some embodiments, cap 300 may be collapsible for deployment and expandable for use. Cap 300 may assume collapsed and expanded configurations using known mechanisms. For example, cap 300 may be self-expandable, or it may expand by some actuation mechanism such as springs.

In an embodiment, the inner surface of cap 300 may include rails 314 that provide a path for medical resection devices, such as snare loops, cautery wires, elastic bands, suction devices, graspers, etc., to effectively grasp and resect tissue from within a patient's body. The illustrated embodiment shows two rails running parallel along the length of the cap 300. It should be understood that the configuration of rails 314 may vary based on intended use and application, for example, the number of rails may vary. Also, rails 314 may extend partially or completely along the length of the cap. In any configuration, rails 314 extend until the distal end of the cap 300 such that a dissection device, such as a cutting wire, running on rails 314 exits from edge 322. Alternatively, rails may run until edge 318 so that the cutting wire can be pulled across opening 312 from front to back.

In some cases, rails 314 may be configured as grooves, which may be similar in function to rails 314. That is, rather than projections that a medical device can ride upon, the grooves may allow a medical device to ride within the grooves and along cap 300.

In a further embodiment, cap 300 may be configured for application of suction through one or more walls, instead of through opening 312, as will be discussed in greater below. In such embodiments, one or more sides 316, 318, 320 and 322 may include a plurality of openings in communication with a suction source. In these instances, e.g., the plurality of openings may be in communication with a port or other connection device, for connection to a separate suction source.

Figure 4A:
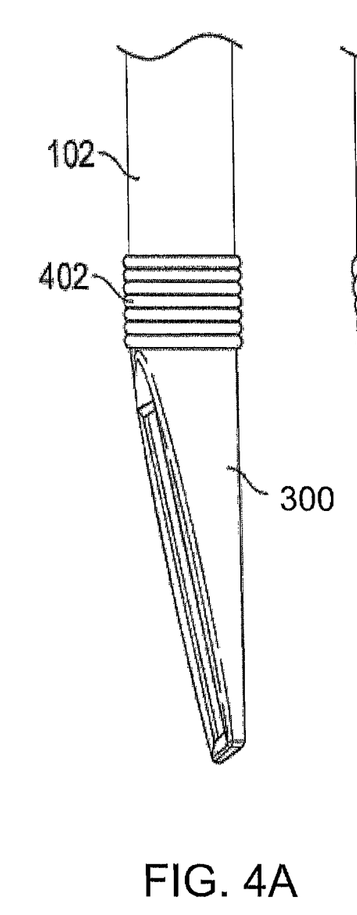
FIGS. 4A and 4B illustrate different positions of an articulating cap of the resection device of FIG. 1, according to a further embodiment of the present disclosure.
Figure 4B:
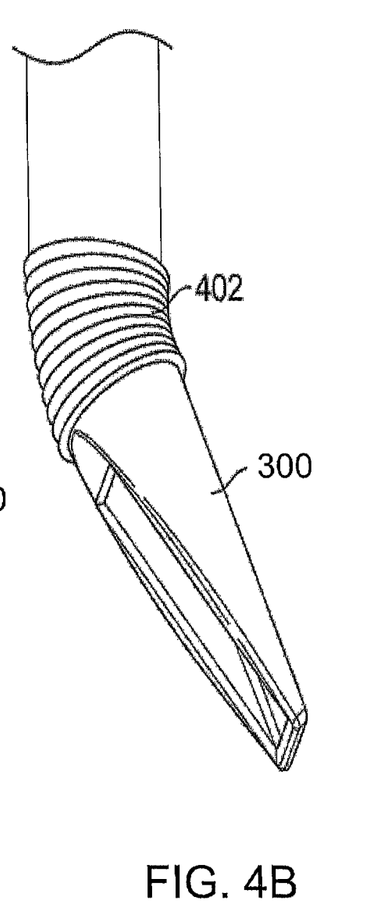

In an embodiment of the present disclosure, the cap 300 may be flexible around its proximal end, as shown in FIGS. 4A and 4B, facilitating effective alignment of the distal end opening 312 with the targeted tissue. As shown, cap 300 may be connected to an elongate member such as the elongate member 102, and the cap 300 may swivel, pivot, and/or rotate around a base 402 in any desired direction by any suitable construction means known in the art. FIGS. 4A and 4B are schematic end views of the cap and elongated member 102 that illustrate such an embodiment.

To facilitate effective movement of cap 300, base 402 may be generally made of a flexible material, such as, e.g., rubber, plastic, or any suitable flexible material known to those in the art. Base 402 may either be integral to the proximal end of the cap 110 or may be a separate member connecting the cap 300 to the elongate member 102. The flexible nature of base 402 may also allow cap 300 to fit on elongate member 102 of varying sizes.

Movement of cap 300 relative elongate member 102 may be achieved through any known mechanism. For example, a set of wires connected to cap 300 may extend to proximal end 106 of the elongate member 102 along the length of the elongate member 102 through a channel (not shown). These wires may be manipulated manually or automatically, allowing a user to selectively position cap 300 in a desired orientation.

In addition, base 402 may include, for example, a stent-like braid or rubber bellows configured to maintain an airtight seal between cap 300 and elongate member 102. In an embodiment, base 402 may be coated with any suitable air tightening sealant.

Figure 5A:
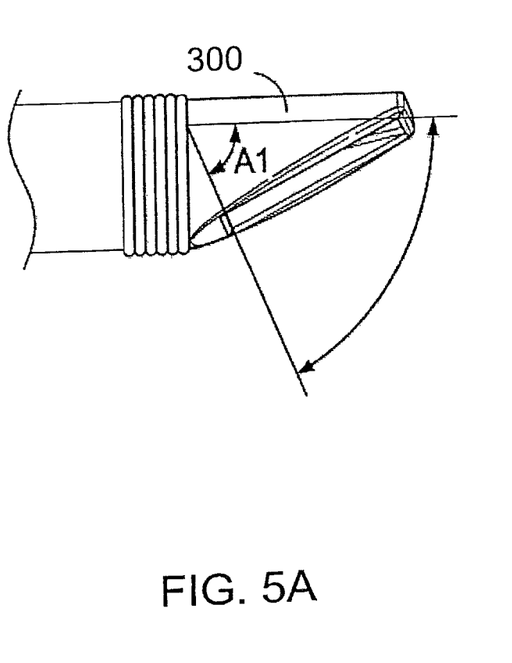
FIGS. 5A and 5B illustrate different angles of view of the articulating cap depicted in FIGS. 4A and 4B.
Figure 5B:
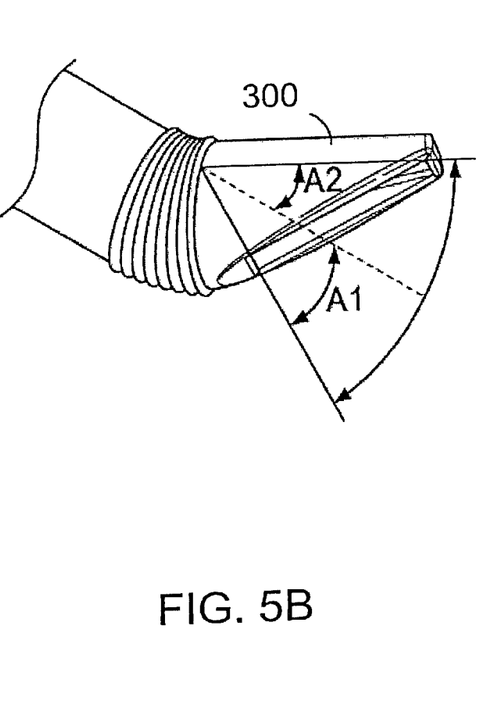

The fact that the cap 300 can flex around its base 402 may increase the angle of view of the resection device 100. Further, the flexibility may allow an operator to center an endoscope's lens upon the target to be observed, to minimize any optical distortions. FIG. 5A depicts cap 300 being parallel to the longitudinal axis of the elongate member 102, and in this configuration, resection device 100 provides an angle A1 as the angle of view. When the cap 300 is diverted in a desired direction by an angle A2, the angle of view of the resection device 100 increases, as shown in FIG. 5B. In addition, the flexion capability rendered by the present disclosure allows the resection device 100 to align the distal end opening of cap 300 with an undesired tissue and ensure that tissue may be drawn into the cap 300 effectively.

Various alternatives of the resection device 100 may be contemplated. For example, the distal end of the cap 110 may not be slant or cut at an angle. In such configurations, at least one portion of one edge of the distal end opening 312 may be straight. In some implementations, the cross-sectional shape of the cap may vary from the proximal end to the distal end. For example, the proximal end may be circular and the distal end may include a hexagonal cross-section.

Cap 300 described in the present disclosure may be utilized in combination with any suitable dissection tool. In an embodiment of the present disclosure, a cutting wire (not shown) may loop around the circumference of the distal end opening 312 and the two ends of the wire may extend along the rails 314 shown in FIG. 3. The wire ends may be connected to control mechanisms that assist in tissue removal. For example, rails may include wire bullets (not shown) that keep the wire taut along the circumference of the distal end opening 312 of the cap 300. In addition to, e.g., wire bullets, the cutting wire may include a tube or sheath heatshrunk over the wire, to ensure the wire is operably connected to rails 314. In embodiments, where the cutting wire is capable of cauterizing tissue, a set of connection wires connected to the ends of the cutting wire may energize the cutting tool by passing electrical energy through the connection wires. The cutting wire may have any suitable cross-section geometry, including, but not limited to, oval, square, rectangular, and the like. Further, an edge of the cutting wire may be sharpened to aid in the resection of tissue. In addition, these connection wires may also pull the wire bullets along a length of distal end opening 312, in order to move the cutting wire through the portion of tissue disposed within cap 300 and the remainder of the patient. Because the cutting wire may lie parallel to the distal end opening 312, pulling the cutting wire proximally allows the cap 110 to grasp and hold flat tissues. In an embodiment, the connection wires may be an extension of the cutting wire itself.

In alternate embodiments, the dissection tool may be a separate device not connected to the cap 300. For example, the dissection device may assume a wire loop shape connected to an arm. Such dissection device may advance through a channel of the elongate member 102 and extend within the cap 300 to perform desired cutting process. Alternatively, the loop may advance along the outer surface of the elongate member 102 with the help of the arm. In such embodiments, the dissection device may advance towards the distal end 304 of the cap 300 using a guide attached to the exterior surface of the elongate member 102. Once the dissection device reaches proximate the distal end opening 312 of the cap 300, the wire may be drawn along the distal end opening 312 of the cap 300, dissecting the tissue drawn into the cap 300. Still further, the dissection tool may be integrated with the medical device, creating a single device for resection procedures.

It should be understood that shape and configuration of the dissection device may vary based on the intended use and application. For example, instead of a circular wire loop, the dissection device may assume other suitable shapes such as hexagonal, semi-circular, etc. The dissection device may include other suitable device such as scalpel, blades, or flat wires. Such devices may slidably traverse on the outer surface of the elongate member 102. In alternate embodiments, the resection device 100 may utilize dissection device having at least one straight edge instead of a cap having a straight edge.

Figure 6A:
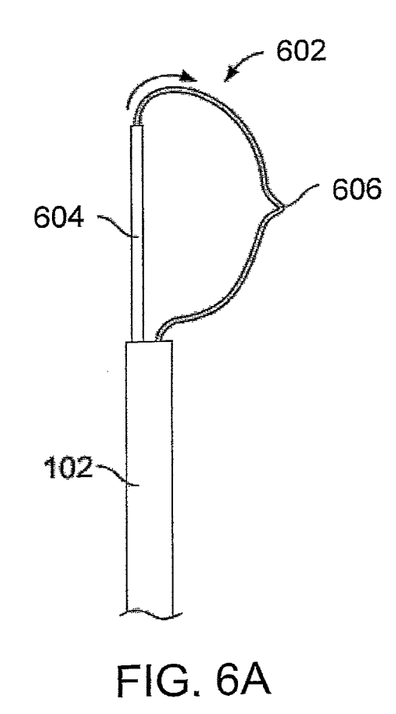
FIGS. 6A-6C illustrate different positions of a resection device according to further embodiments of the present disclosure.
Figure 6B:
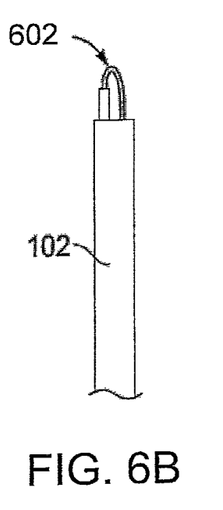
Figure 6C:
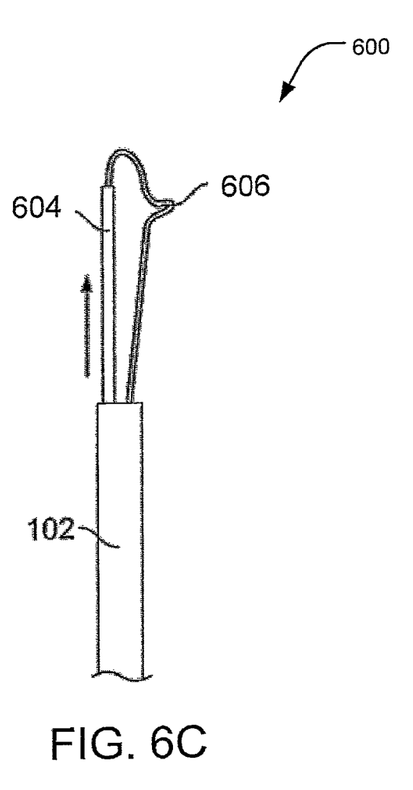

FIGS. 6A-6C illustrate an embodiment of a cutting device 600 that utilizes a modified wire loop 602 for complete tissue resection. The wire loop 602 includes a semi-circular loop 606 that assists in removing semi-circular sections of tissue. In addition, the wire loop 602 may include a straight rigid arm 604. The two ends of the semicircular loop 606 are connected to the ends of arm 604. In addition, the proximal end of the wire loop 602 may be connected to a handle or a similar elongate device for insertion or retraction purposes. The semicircular loop 606 is similar to snares known in the art and will not be discussed in detail. The arm 604 may be made of suitable rigid material such as metal, alloys, polymer, etc.

In use, the wire loop 602 having the semicircular loop 606 and the arm 604 may extend from a distal end of the elongate member 102, as shown in FIG. 6B. Wire loop 602 may be inserted through a working channel of the elongate member 102. The semicircular loop 606 may remain compressed during insertion and retraction process, as shown in FIG. 6C. Once completely deployed, the wire loop 602 can expand to form a semicircular loop, as shown in FIG. 6A.

The modified wire loop 602 may remove semicircular sections of a desired tissue. Such a cutting device may be helpful where desired tissue is generally circular in shape. For resection purpose, the straight arm 604 may be pressed down generally along the diameter of the desired tissue and subsequently, the wire loop 602 may be retracted into the elongate member 102 to resect a semicircular section of the tissue.

Figure 7:
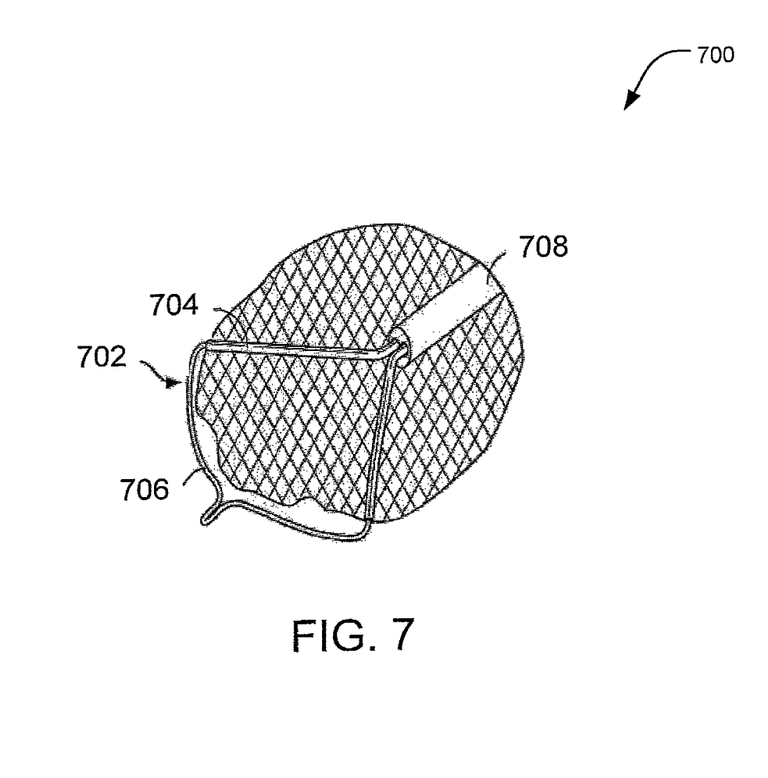
FIG. 7 illustrates an alternate embodiment of a resection device, according to the principles of the present disclosure.

FIG. 7 depicts an alternate embodiment of a cutting device 700, in accordance with the principles of the present disclosure. In the depicted embodiment, wire loop 702 may include two rigid arms 704, and a quarter-circular (or any other desired segment of a circle) loop 706 is connected between the distal ends of the arms 704. In one configuration, the two arms 704 may be disposed perpendicularly to each other such that the loop 706 forms a quarter circle. This configuration of the wire loop 702 allows removing quarter circular tissue sections. It should be understood that the angle between the arms may vary based on the intended use and application. In addition, the proximal ends of the arms 704 are connected to a handle 708 through which a user may operate the wire loop 702.

In an embodiment, the cutting device 700 may assume a compressed configuration within the elongate member 102 for insertion and retraction purposes. Once completely deployed, the device 700 may extend from the distal end of the elongate member 102 and expand. In the expanded configuration, the arms 704 diverge at angle such as 90 degrees and the quarter-circular loop 706 may remain taut between the arms 704, as shown.

In each of the embodiments illustrated in FIGS. 6 and 7, the described wire loops may be energized by passing electrical energy through the loop. Moreover, the electrical energy may be sufficient to cauterize the tissue swiftly. The cauterizing wire loop may be mono-polar where high frequency electrical current is passed from a single electrode and the patient's body serves as ground or bipolar where high frequency electrical current is passed through the targeted tissue from one electrode to another. It will be understood that instead of electrical energy, any other form of energy now known or known in the future may be supplied to the describe cutting loops to resect the targeted tissue from the organ wall. For example, high heat energy may be supplied, enabling the cutting loops to burn the targeted tissue from the organ wall. Similarly, other energy sources such as radio frequency, laser, harmonics, and/or hydro-dissection sources may be considered without departing from the scope of the present disclosure.

The following section sets out an exemplary method for resecting lesions or any other undesired tissue from a patient's body. A typical location for a resection of this sort may be the stomach, and that location will be discussed here. As will be understood by those in the art, other patient locations would be equally suitable. Either a percutaneous incision is made to access the gastrointestinal tract, or the resection device 100 may be inserted through a natural opening, such as the mouth or anus.

Figures 8A, 8B, 8C:
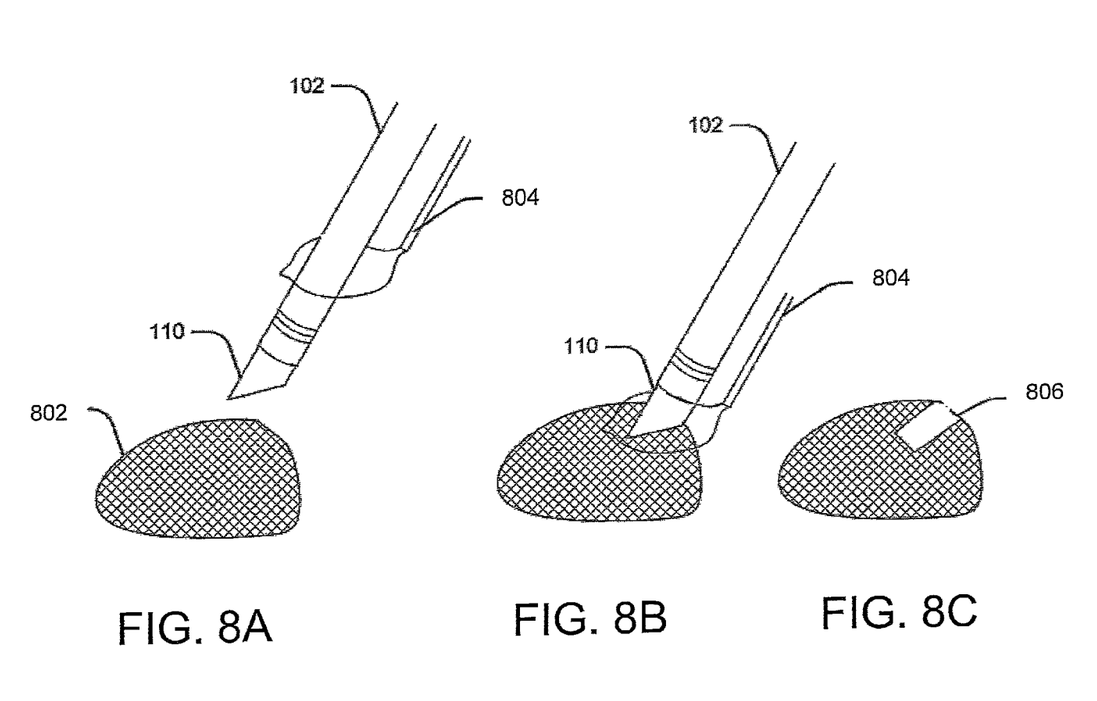
FIGS. 8A-8D illustrate an exemplary method for resecting tissue using the resection device of FIG. 1 according to an embodiment of the present disclosure.

As shown in FIG. 8A, the resection device 100 may be directed towards targeted tissue, e.g., a lesion 802 present on, e.g., a mucosal wall. A steering mechanism may be incorporated in resection device 100 (with controls in the handle) to guide and urge the device within a body cavity. A light source and a camera (not shown) may be inserted in the elongate member's lumen to direct resection device 100 within the stomach, and to identify targeted tissue. Various identification techniques may be employed. For example, a biomarker or dye may be applied around the gastrointestinal tract. Cancerous lesions emit a different wavelength when light falls on them, allowing operators to easily detect them.

As shown, the distal end opening 312 of, e.g., cap 300 may be placed over the lesion 802. In case the lesion is situated at an unreachable position within the body, cap 300 may be selectively oriented, as described in connection with FIGS. 4A-4B, to attain contact with the lesion 802.

A dissection tool 804 may be introduced towards the distal end of the cap 300. Here, dissection tool 804 assumes a cutting wire loop form that is guided along the outer surface of elongate member 102. As shown, the dissection tool 804 may rest along the distal end opening 312 of the cap 300 on the lesion 802, as shown in FIG. 8B. In another embodiment, dissection tool 804 may advance through rails 314 disposed on the inner surface of the cap 300, as discussed in connection with FIG. 3.

Subsequently, a grasping device, such as suction pump, graspers, forceps, pincers, or any other such medical device that can draw the lesion 802 into the cap cavity, is activated. In an embodiment of the present disclosure, a suction device, connected to a working channel of the elongate member 102, introduces suction force that draws the lesion 802 into the cap 300. In one embodiment, if the lesion is too flat along the esophageal wall, the lesion may be injected with a solution, e.g., a saline solution or a gel, to create a buffer layer, e.g., a bleb, between the lesion and that wall. With the lesion sufficiently raised off the esophagus wall, suction may be more easily accomplished.

Subsequently, the suction device may be powered off or removed, and a suitable imaging device (not shown) may be introduced into the elongated member 102, along with an illumination device (not shown), allowing a physician to closely examine the lesion, and to determine whether the lesion requires resection. Various other known techniques may be employed for this determination, without departing from the scope of the present disclosure.

When targeted tissue is identified, the distal end of the dissection tool 804 may extend beyond the distal end of cap 300, and be positioned substantially parallel to the distal opening of the cap 300. If capable of cautery, the dissection tool 804 may be energized and dissection tool 804 may be pulled proximally, so that loop begins closing up, reducing the loop's diameter and trapping lesion 802. With the lesion 802 drawn into cap 300, dissection tool 804 may be in a position to cut through the lesion near its base. Subsequent pulling may contract loop further and may finally dissect the tissue 802. The resection device dissects the tissue in the cross-sectional shape of the cap 300, which is rectangular in the illustrated embodiment. Consequently, the device 100 removes a rectangular section 806 of the lesion 802, as shown in FIG. 8C.

Figure 8D:
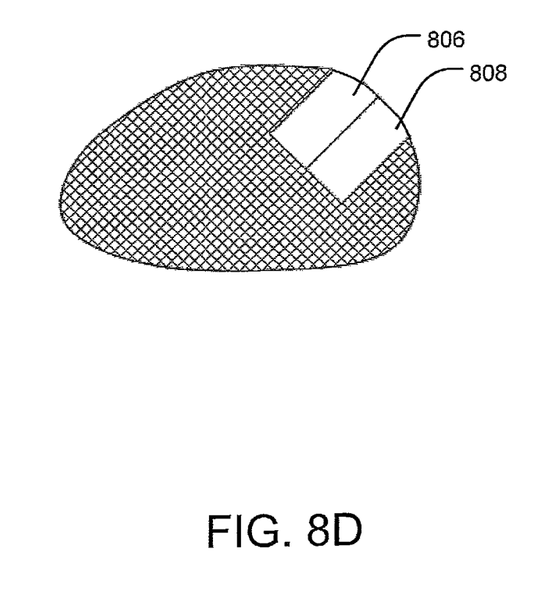

As lesion size may be greater than the distal end opening 312 of the cap 300, subsequent dissection by resection device 100 may be required. In such situations, the resection device 100 may be repositioned to remove adjacent lesion sections. To ensure complete lesion resection, one of the straight edges of the cap 300 may be aligned with one of the straight edges from the removed section 806. The tissue cutting process discussed above may be repeated to remove another rectangular portion 810 of the lesion 802, allowing for subsequent cuts to be tessellated next to one another, as shown in FIG. 8D. Adjacent sections may be continually removed without leaving behind islands of tissue.

It should be understood that the resected tissue shape varies based on the cross-section of cap's distal end opening. Accordingly, the shape of the resected potion may be square, rhombic, octagon, triangular, etc., so that at least one portion of one edge of a distal end opening is straight.

In alternate embodiments, the resection procedure may instead utilize a modified a cutting loop, as discussed in connection with FIGS. 6 and 7. In such embodiments, once the distal end of the elongate member 102 reaches proximate the lesion 802, wire loop 602 or 702, which may be initially compressed to pass through a suitable introduction sheath, extends from the distal end of the elongate member 102. The cutting device may be directed towards the lesion using a control mechanism attached to the proximal end of the elongate member 102, if required. As the cutting device advances out of the elongate member 102, it expands to form a semi-circular loop 606 or a quarter-circular loop 706.

If wire loop 602 is utilized, the rigid arm 604 may be pressed down across the diameter of the lesion, and the semi-circular loop 606 may encompass rest on a semicircular section of lesion 802. Retracting the wire loop 602 into the elongate member 102 may result in cutting through a semi-circular section of the lesion encompassed by the loop 606. The remaining semi-circular lesion may be resected by aligning the arm 604 with the straight line of dissection and aligning the loop 606 with the other side of the diameter.

If cutting wire loop 702 is employed, the arms 704 may be pressed down against the lesion such that the point where the arms 704 meet may substantially coincide with the center of the lesion. As previously discussed, loop 706 may resect a quarter-circular (or any other suitable segment of a circle) section of the lesion. Subsequent resection may be accomplished by aligning the arms 704 with a straight side of the resected portion and repeating the process to remove the remaining portions of the lesion.

In each of the embodiments described in connection with FIGS. 6 and 7, subsequent removal of lesion may not require repositioning of the entire resection device. Instead, the wire loop 602 or 702 may be retracted into the elongate member 102. The elongate member 102 or the loop may be rotated such the straight arms 604 or 704 align with straight line of dissection of the previous cut for subsequent cutting.

In embodiments where the cutting device includes wire loops 602 or 702, it should be understood that the diameter of the loop 606 or 706 may be modified to completely encompass semicircle, quarter-circle, or any suitable portion of a lesion, respectively.

Once the lesion is resected, device 100 may carry out any number of procedures to excise the resected matter. For example, resection device 100 may extract the lesion or morcellate it and then extract it. For extraction, any retrieval device presently known or later developed may be employed. In one embodiment, the lesion may be extracted with the help of suction force applied at proximal end 106 of resection device 100. In another embodiment, a basket, a grasper, or pincers may be used.

Embodiments of the present disclosure may be used in any medical or non-medical procedure, including any medical procedure where monitoring of an organ's activity is desired. In addition, at least certain aspects of the aforementioned embodiments may be combined with other aspects of the embodiments, or removed, without departing from the scope of the disclosure.

Other embodiments of the present disclosure will be apparent to those skilled in the art from consideration of the specification and practice of the embodiments disclosed herein. It is intended that the specification and examples be considered as exemplary only, with a true scope and spirit of the invention being indicated by the following claims.

What is claimed is:

1. A resection device comprising:
an elongate member having a proximal end, a distal end, and a longitudinal axis between the proximal end and the distal end;
a cap at the distal end of the elongate member, wherein the cap includes an opening in communication with a channel extending between the proximal and distal ends of the elongate member; and
a flexible portion between the proximal end of the elongate member and the opening, wherein an angle between the longitudinal axis of the elongate member and a plane of the opening is changeable, the opening is moveable about the flexible portion, and the opening includes at least one straight edge, wherein, when the flexible portion is in an unbent position, the opening faces to a side of the device and distal of the device.

2. The resection device of claim 1, wherein the plane is angled relative to a longitudinal axis of the cap.

3. The resection device of claim 1, further comprising a cutting device configured to cut tissue adjacent the cap.

4. The resection device of claim 1, further comprising a flexible portion disposed between the distal end of the elongate member and the opening.

5. The resection device of claim 3, wherein the cutting device includes a wire spanning a width of the opening.

6. The resection device of claim 5, wherein the wire is configured to conduct energy to the tissue.

7. The resection device of claim 1, wherein the cap includes a flexible base.

8. The resection device of claim 7, wherein the cap moves relative to the elongate member about the base.

9. The medical device of claim 1, wherein the opening moves relative to the channel.

10. A device comprising:
an elongate member having a proximal end, a distal end, a channel extending between the proximal end and the distal end, a distal portion, an intermediate portion proximal to the distal portion and with flexibility greater than a flexibility of the distal portion, and a proximal portion proximal to the intermediate portion,
wherein the distal portion of the elongate member includes an opening adapted to be placed proximate tissue, wherein the opening includes at least one straight edge, and wherein the opening is disposed in a plane that is angled relative to a longitudinal axis of the device, and the opening moves relative to the proximal portion of the elongate member about the intermediate portion, wherein, when the intermediate portion is in an unbent position, the opening faces to a side of the device and distal of the device.

11. The device of claim 10, wherein the distal portion includes a cap that defines the opening with the at least one straight edge, wherein the cap includes a cavity in communication with the opening.

12. The device of claim 10, wherein the opening is one of rectangular, square, or rhombic in shape.

13. The device of claim 10, wherein the opening is side facing and distal facing.

14. The device of claim 10, further comprising a cutting device configured to cut tissue along at least one straight line of dissection.

15. The device of claim 14, wherein the cutting device includes a wire spanning the opening.

16. The device of claim 10, wherein the distal portion of the elongate member is configured to pivot relative to a remainder of the elongate member.

17. The device of claim 10, wherein the opening moves relative to the channel.

18. A method for resecting tissue from a body, the method comprising:
inserting a device into a body cavity, the device including:
   an elongate member having a proximal portion, a distal end, and a channel extending therebetween,
   a cap at the distal end of the elongate member, wherein the cap includes a distal end opening, wherein the distal end opening includes at least one straight edge, and
   a flexible portion between the proximal portion of the elongate member and the opening, wherein the distal end opening is angled relative to a longitudinal axis of the elongate member and is moveable relative to a longitudinal axis of the elongate member about the flexible portion, wherein, when the flexible portion is in an unbent position, the distal end opening faces a side of the device and distal of the device; and
   a cutting device configured to cut tissue, the cutting device being adapted for placement adjacent a distal-most edge of the distal end;
pulling the tissue into the distal end opening; and
resecting the tissue with the cutting device.

19. The method of claim 18, wherein resecting the tissue includes moving the cutting device relative to the distal end opening.

20. The method of claim 18, wherein the cap includes a flexible base, and the cap moves relative to the elongate member about the base.

* * * * *